(12) United States Patent
Liu et al.

(10) Patent No.: US 9,763,969 B2
(45) Date of Patent: Sep. 19, 2017

(54) TREATMENT OF INFLAMMATORY CONDITIONS WITH HYALURONAN DISACCHARIDE

(71) Applicant: CEDARS-SINAI MEDICAL CENTER, Los Angeles, CA (US)

(72) Inventors: George Liu, Los Angeles, CA (US); Pierre Kyme, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/782,269

(22) PCT Filed: Apr. 3, 2014

(86) PCT No.: PCT/US2014/032893
§ 371 (c)(1),
(2) Date: Oct. 2, 2015

(87) PCT Pub. No.: WO2014/165713
PCT Pub. Date: Oct. 9, 2014

(65) Prior Publication Data
US 2016/0022715 A1    Jan. 28, 2016

Related U.S. Application Data

(60) Provisional application No. 61/808,063, filed on Apr. 3, 2013.

(51) Int. Cl.
*A61K 31/7016*    (2006.01)
*A61K 38/47*    (2006.01)
*C12N 9/26*    (2006.01)

(52) U.S. Cl.
CPC .......... *A61K 31/7016* (2013.01); *A61K 38/47* (2013.01); *C12N 9/2474* (2013.01); *C12Y 302/01035* (2013.01)

(58) Field of Classification Search
CPC ... A61K 31/7016; A61K 38/47; A61K 31/728
USPC .......................................................... 514/53
See application file for complete search history.

(56) References Cited

U.S. PATENT DOCUMENTS

| | | | |
|---|---|---|---|
| 5,830,882 A | 11/1998 | Falk et al. | |
| 7,132,412 B2 | 11/2006 | Petrigni et al. | |
| 8,202,517 B2 | 6/2012 | Bookbinder et al. | |
| 2002/0086852 A1 | 7/2002 | Cantor et al. | |
| 2006/0100178 A1 | 5/2006 | Masatsuji et al. | |
| 2007/0099867 A1 | 5/2007 | Asari et al. | |
| 2010/0172892 A1 | 7/2010 | Uvarkina et al. | |
| 2010/0323983 A1 | 12/2010 | Moutet et al. | |
| 2011/0263521 A1 | 10/2011 | Moutet et al. | |
| 2013/0059769 A1 | 3/2013 | Turley | |
| 2013/0072452 A1 | 3/2013 | Lin et al. | |

FOREIGN PATENT DOCUMENTS

| | | |
|---|---|---|
| JP | 2007291133 A | 11/2007 |
| WO | 2008047779 A1 | 4/2008 |
| WO | 2011156445 A1 | 12/2011 |
| WO | 2014165713 A2 | 6/2015 |

OTHER PUBLICATIONS

International Search Report and Written Opinion for International Application No. PCT/US14/32893, dated Apr. 13, 2015, 11 pages.
IPRP for International Application No. PCT/US14/32893, dated Oct. 15, 2015, 8 pages.
Li, S. et al., Hyaluronan binding and degradation by *Streptococcus agalactiae* hyaluronate lyase*, The Journal of Biological Chemistry, 2001, 276(44):41407-41416.
Ponnuraj, K. et al., Mechanism of hyaluronan binding and degradation: structure of *Streptococcus pneumoniae* hyaluronate lyase in complex with hyaluronic acid disaccharide at 1.7 A resolution, JMB,2000, 299:885-895.
Pritchard, D.G. et al., Characterization of the Group B streptococcal hyaluronate lyase, Archives of Biochemistry and Biophysics, 1994, 315(2):431-437.
EP 14780170.8 Partial Supplemental Search Report dated Feb. 17, 2017; 7 pages.
Noble, P.W. Hyaluronan and its catabolic products in tissue injury and repair. Matrix Biology (2002). 21:25-29.

*Primary Examiner* — Scott Long
*Assistant Examiner* — Paul Martin
(74) *Attorney, Agent, or Firm* — Hema Vakharia-Rao; Nixon Peabody LLP

(57) ABSTRACT

The present invention describes compositions and related methods and kits for treating a variety of inflammatory conditions and infections. The therapeutic compositions include certain hyaluronidases capable of generating hyaluronan disaccharides when combined with hyaluronan, and/or the hyaluronan disaccharides themselves, and/or inflammatory hyaluronidase inhibitors. The invention further discloses the use of hyaluronidase inhibitors to treat certain infections in an individual.

6 Claims, 15 Drawing Sheets

TREATMENT OF INFLAMMATORY CONDITIONS WITH HYALURONAN DISACCHARIDE

CROSS-REFERENCE TO RELATED APPLICATIONS

This application is the National Phase of International Application PCT/US2014/032893, filed Apr. 3, 2014, which designated the U.S. and that International Application was published under PCT Article 21(2) in English. This application also claims the benefit under 35 U.S.C. §119(e) to U.S. Provisional Application No. 61/808,063, filed on Apr. 3, 2013, which is incorporated herein by reference in its entirety.

STATEMENT REGARDING FEDERALLY SPONSORED RESEARCH OR DEVELOPMENT

This invention was made with government support under Grant No. AI103839 awarded by National Institutes of Health. The government has certain rights in the invention.

FIELD OF THE INVENTION

The present invention generally relates to the prevention and treatment of inflammatory conditions and infections.

BACKGROUND

The following description includes information that may be useful in understanding the present invention. It is not an admission that any of the information provided herein is prior art or relevant to the presently claimed invention.

One important host defense mechanism against pathogens is linking pathogen induced tissue damage to activation of inflammatory immune cascades. In such cases, connective tissue damage generates hyaluronan degradation fragments that efficiently bind to and activate the host's Toll-like receptor (TLR) immune pathway that is designed mainly to detect microbial invaders. This strategy should render stealth almost impossible for any pathogenic organism aiming to infiltrate deep tissues. However, successful pathogens can counter this strategy by tactically exploiting key features of their secreted hyaluronidase isoforms.

Among the bacterial hyaluronidases that have been characterized, two general hyaluronan fragmentation patterns have been described. Hyaluronidases from the *streptococcal* species *S. pneumoniae* and Group B *Streptococcus* (GBS), also known as *Streptococcus agalactiae*, produce disaccharides only. In contrast, evidence suggests that hyaluronidases expressed by *Streptomyces* and phylogenetically related *P. acnes*, produce larger fragments, similar in size to those generated by the immune-activating human hyaluronidase. Importantly, the disaccharides generated by *streptococci* do not activate immune defenses, whereas the larger hyaluronan fragments produced by *Streptomyces* and *P. acnes* appear to be highly immunogenic and pro-inflammatory. Considering all of these immunogenic, pro-inflammatory, and immune evasion effects, the inventors developed a number of therapeutic strategies described below.

SUMMARY OF THE INVENTION

In various embodiments, the invention teaches a method for treating and/or inhibiting an inflammatory condition in a subject. In some embodiments, the method includes administering a therapeutically effective amount of a composition that includes hyaluronan disaccharide to the subject. In some embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In certain embodiments, the inflammatory condition is acne. In some embodiments, when the inflammatory condition is acne, the composition is administered topically. In certain embodiments, the inflammatory condition is pulmonary fibrosis. In some embodiments, when the inflammatory condition is pulmonary fibrosis, the composition is administered into the respiratory system.

In various embodiments, the invention teaches a method for treating and/or inhibiting an inflammatory condition in a subject. In some embodiments, the method includes administering to the subject a therapeutically effective amount of a composition that includes a hyaluronidase that is capable of producing a hyaluronan disaccharide when combined with a quantity of hyaluronan. In certain embodiments, the hyaluronidase produces the hyaluronan disaccharide via processive degradation of a longer chain of hyaluronan. In certain embodiments, the hyaluronidase is produced by an organism selected from the group consisting of Group B *Streptococcus* (GBS), Group A *Streptococcus, S. aureus, S. pneumoniae, E. faecalis*, and *P. prevotii*. In certain embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In certain embodiments, the inflammatory condition is acne. In some embodiments, when the inflammatory condition is acne, the composition is administered topically. In certain embodiments, the inflammatory condition is pulmonary fibrosis. In some embodiments, when the inflammatory condition is pulmonary fibrosis, the composition is administered into the respiratory system.

In various embodiments, the invention teaches a method for treating and/or inhibiting an infection caused by a pathogen in a subject. In some embodiments, the method includes administering a therapeutically effective amount of a composition that inhibits a hyaluronidase produced by the pathogen to the subject. In certain embodiments, the infection is caused by an organism selected from the group consisting of Group B *Streptococcus* (GBS), Group A *Streptococcus, S. aureus, S. pneumoniae, E. faecalis, P. prevotii, S. mutans*, and *C. difficile*. In some embodiments, the pathogen is GBS and the composition includes a GBS hyaluronidase inhibitor.

In various embodiments, the invention teaches a composition for treating and/or inhibiting an inflammatory condition in a subject. In some embodiments, the composition includes a hyaluronan disaccharide. In some embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In certain embodiments, the inflammatory condition is acne. In some embodiments, when the inflammatory condition is acne, the composition is formulated for topical administration. In certain embodiments, the inflammatory condition is pulmonary fibrosis. In some embodiments, when the inflammatory condition is pulmonary fibrosis, the composition is formulated for administration into the respiratory system.

In various embodiments, the invention teaches a composition for treating and/or inhibiting an inflammatory condition in a subject. In some embodiments, the composition includes a hyaluronidase capable of producing a hyaluronan disaccharide when combined with a quantity of hyaluronan. In certain embodiments, the hyaluronidase produces hyaluronan disaccharide via processive degradation of a longer chain of hyaluronan. In some embodiments, the hyaluronidase is produced by an organism selected from the group consisting of: Group B *Streptococcus* (GBS), Group A *Streptococcus, S. aureus, S. pneumoniae, E. faecalis,* and *P. prevotii*. In certain embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In certain embodiments, the inflammatory condition is acne. In some embodiments, when the inflammatory condition is acne, the composition is formulated for topical administration. In some embodiments, the inflammatory condition is pulmonary fibrosis. In certain embodiments, when the inflammatory condition is pulmonary fibrosis, the composition is formulated for administration into the respiratory system.

In various embodiments, the invention teaches a composition for treating and/or inhibiting an inflammatory condition in a subject. In some embodiments, the composition includes an inhibitor of an inflammatory hyaluronidase. In certain embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In some embodiments, the inflammatory condition is acne. In certain embodiments, when the inflammatory condition is acne, the composition is formulated for topical administration. In certain embodiments, the inflammatory condition is pulmonary fibrosis. In some embodiments, when the inflammatory condition is pulmonary fibrosis, the composition is formulated for administration into the respiratory system.

In various embodiments, the invention teaches a composition for treating and/or inhibiting an inflammatory condition in a subject. In some embodiments, the composition includes a hyaluronan disaccharide and a hyaluronidase capable of producing a hyaluronan disaccharide when combined with a quantity of hyaluronan, and optionally an inflammatory hyaluronidase inhibitor. In certain embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In some embodiments, the inflammatory condition is acne. In some embodiments, when the inflammatory condition is acne, the composition is formulated for topical administration. In some embodiments, the inflammatory condition is pulmonary fibrosis. In certain embodiments, when the inflammatory condition is pulmonary fibrosis, the composition is formulated for administration into the respiratory system.

In various embodiments, the invention teaches a composition for treating and/or inhibiting an infection in an individual caused by a pathogen. In some embodiments, the composition includes an inhibitor capable of inhibiting a hyaluronidase produced by the pathogen. In some embodiments, the pathogen is selected from the group consisting of: Group B *Streptococcus* (GBS), Group A *Streptococcus, S. aureus, S. pneumoniae, E. faecalis, P. prevotii, S. mutans,* and *C. difficile*. In certain embodiments, the pathogen is GBS and the inhibitor is a GBS hyaluronidase inhibitor.

In various embodiments, the invention teaches a kit for treating and/or inhibiting an inflammatory condition in a subject. In some embodiments, the kit includes a composition including a hyaluronan disaccharide; and instructions for the use thereof to treat and/or inhibit an inflammatory condition in the subject. In certain embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In some embodiments, the inflammatory condition is acne. In certain embodiments, when the inflammatory condition is acne, the composition is formulated for topical administration. In some embodiments, the inflammatory condition is pulmonary fibrosis. In certain embodiments, when the inflammatory condition is pulmonary fibrosis, the composition is formulated for administration into the respiratory system.

In various embodiments, the invention teaches a kit for treating and/or inhibiting an inflammatory condition in a subject. In some embodiments, the kit includes a hyaluronidase capable of producing a hyaluronan disaccharide when combined with a quantity of hyaluronan; and instructions for the use thereof to treat and/or inhibit an inflammatory condition in the subject. In some embodiments, the inflammatory condition is selected from the group consisting of: pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, and inflammation due to tissue injury. In certain embodiments, the inflammatory condition is acne. In some embodiments, when the inflammatory condition is acne, the composition is formulated for topical administration. In certain embodiments, the inflammatory condition is pulmonary fibrosis. In some embodiments, when the inflammatory condition is pulmonary fibrosis, the composition is formulated for administration into the respiratory system.

In various embodiments, the invention teaches a kit for treating and/or inhibiting an infection in a subject caused by a pathogen. In some embodiments, the kit includes a composition including a hyaluronidase inhibitor capable of inhibiting a hyaluronidase produced by the pathogen; and instructions for the use thereof to treat and/or inhibit an infection in the subject. In some embodiments, the pathogen is GBS and the composition includes a GBS hyaluronidase inhibitor.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
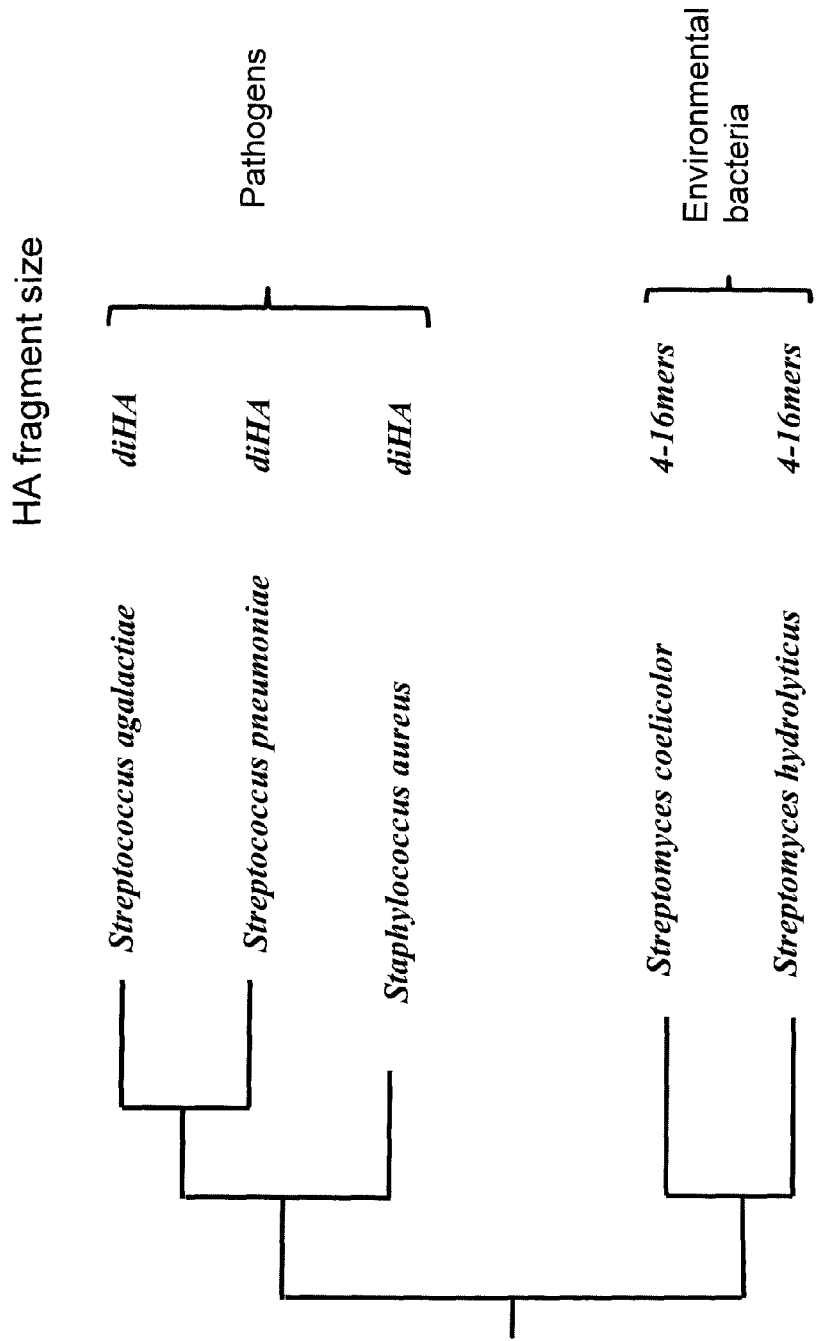
FIG. 1 depicts, in accordance with an embodiment of the invention, a phylogenetic tree based on the deduced amino acid sequences, showing the relatedness of secreted Gram-positive bacterial hyaluronidases.
Figure 2:
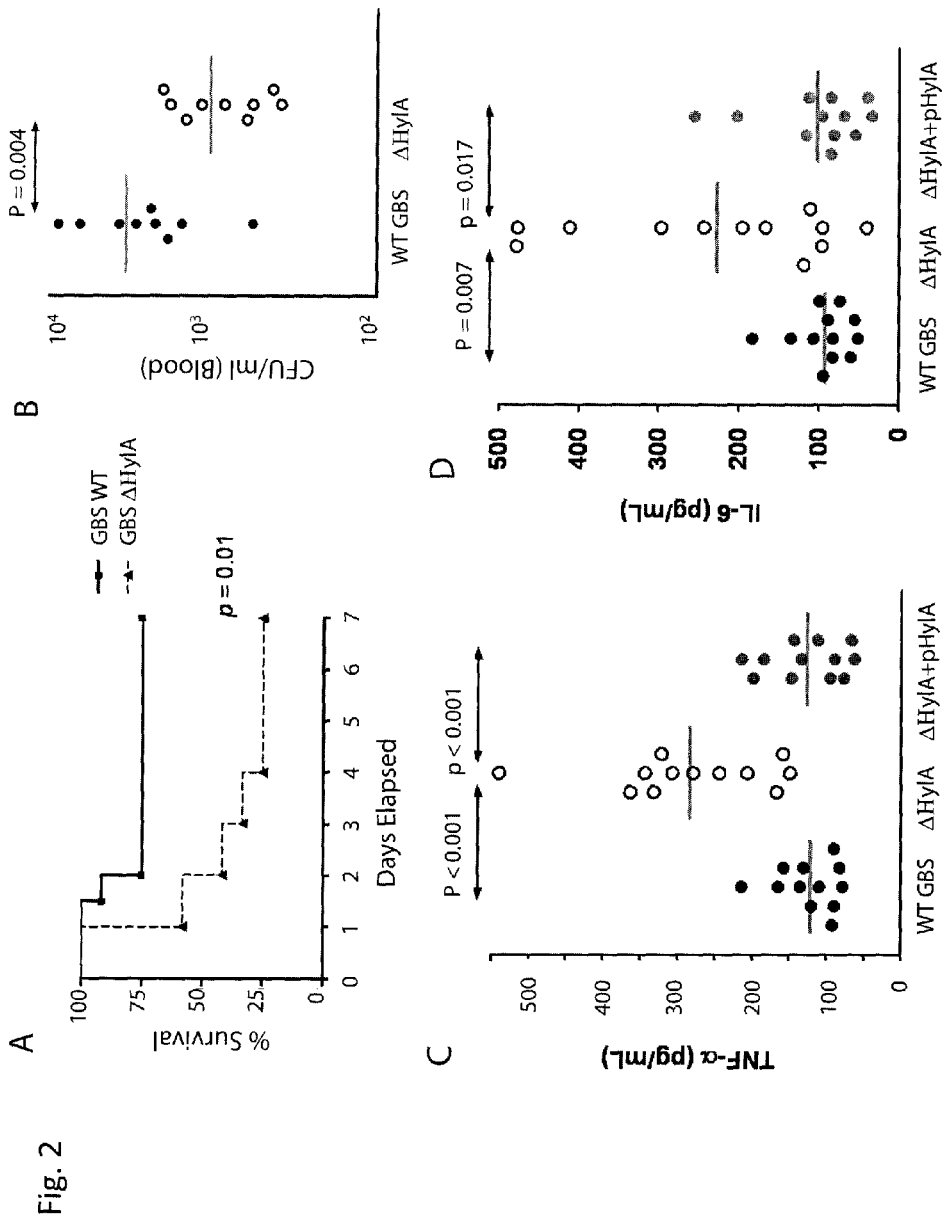
FIG. 2 depicts, in accordance with an embodiment of the invention, in vivo anti-inflammatory properties of GBS hyaluronidase. GBS lacking hyaluronidase induces higher host mortality in a systemic infection model (A), is more readily cleared by the host (B), and induces higher levels of pro-inflammatory cytokines (C and D).
Figure 3:
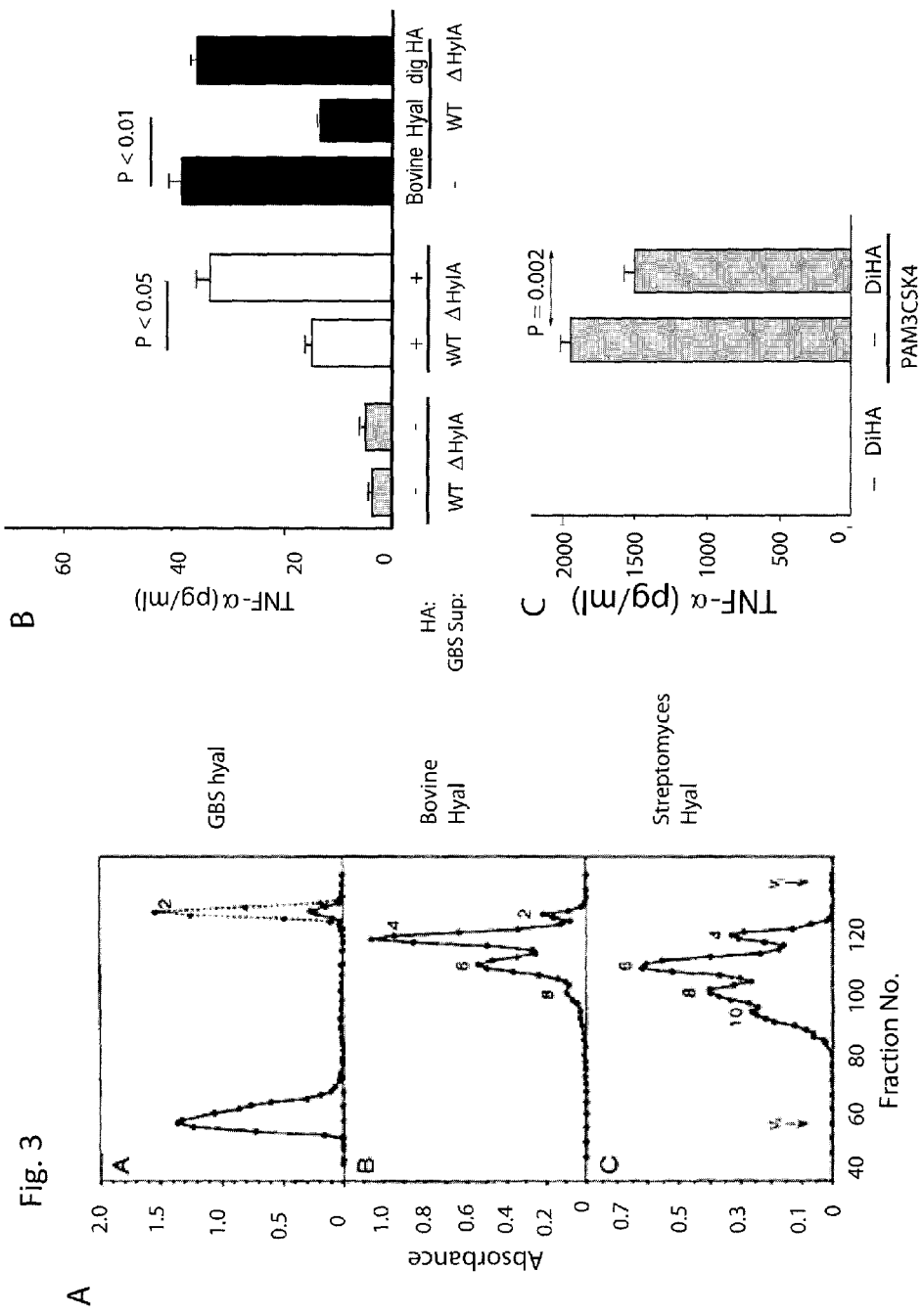
FIG. 3 depicts, in accordance with an embodiment of the invention, in vitro anti-inflammatory properties of GBS hyaluronidase. A. Bio-Gel P-4 chromatography of hyaluronidase digestion mixture following digestion with GBS, bovine testis, or *Streptomyces hyaluronlyticus* hyaluronidase. B. Digestion of HA by GBS hyaluronidase leads to suppressed inflammation. C. HA disaccharide inhibits Pam3csk4 induced TNFα secretion.
Figure 4:
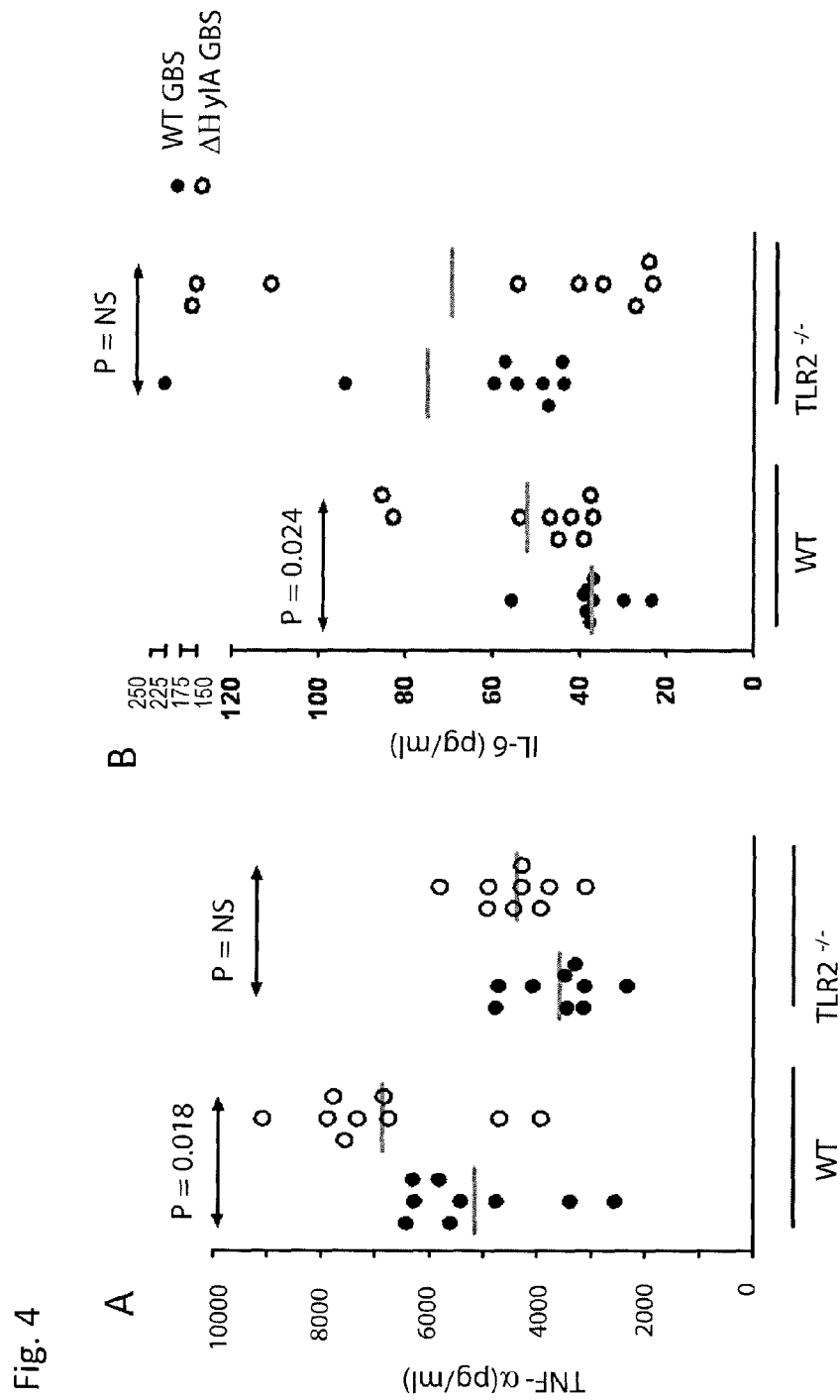
FIG. 4 depicts, in accordance with an embodiment of the invention, anti-inflammatory function of GBS hyaluronidase is TLR-2 dependent.
Figure 5:
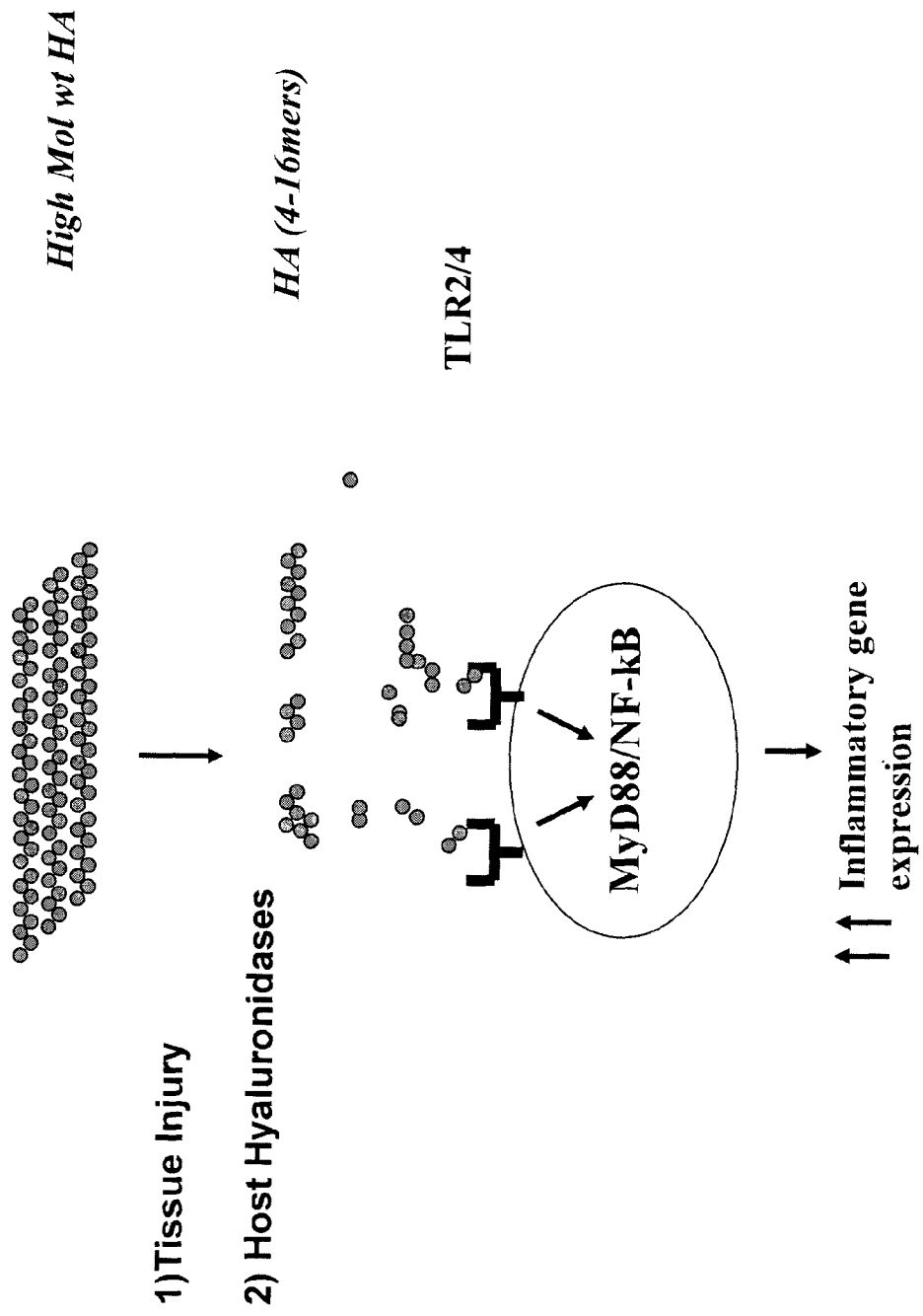
FIG. 5 depicts, in accordance with an embodiment of the invention, hyaluronan breakdown products induce immune cell activation during tissue injury.
Figure 6:
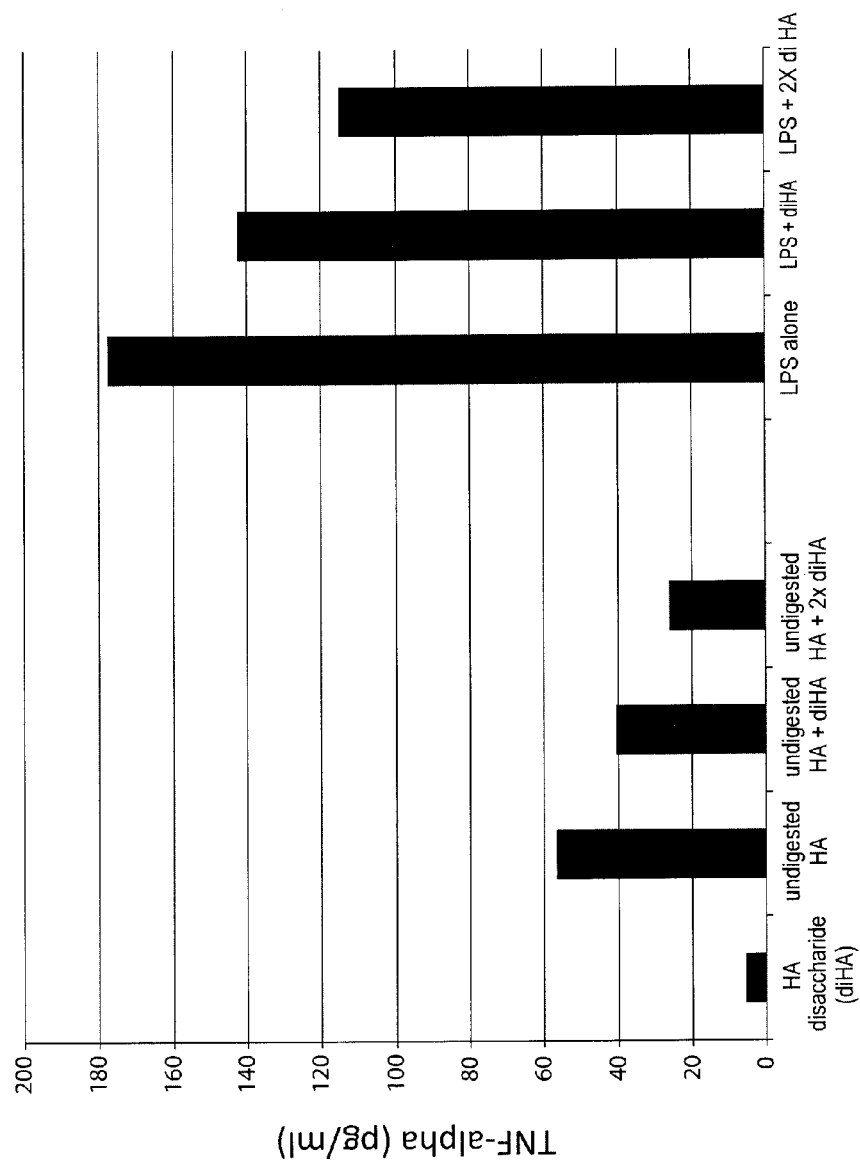
FIG. 6 depicts, in accordance with an embodiment of the invention, hyaluronan disaccharide has an anti-inflammatory property. Hyaluronan disaccharide was co-incubated with LPS or undigested hyaluronan in a macrophage stimulation assay. Hyaluronan disaccharide reduces TNF-α induction by LPS or undigested hyaluronan.
Figure 7:
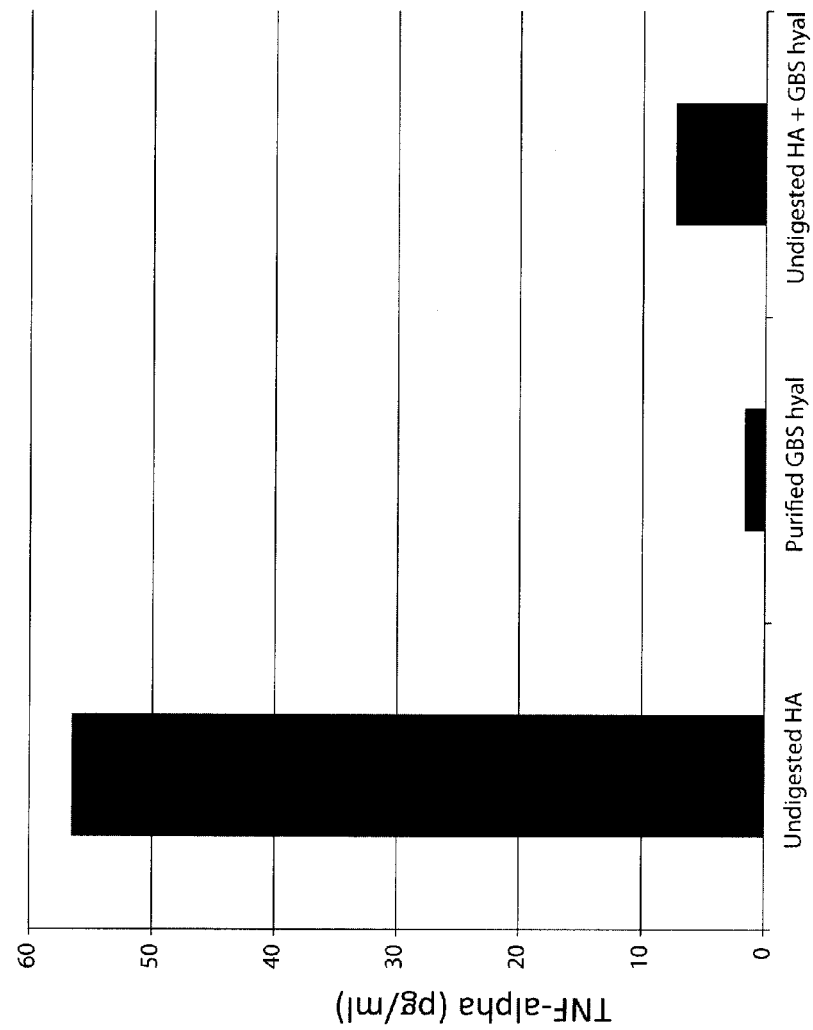
FIG. 7 depicts, in accordance with an embodiment of the invention, Group B *streptococcal* hyaluronidase has an anti-inflammatory property. Hyaluronan was predigested with purified GBS hyaluronidase or PBS, and then transferred to a culture of bone marrow derived macrophages. Prior degradation of hyaluronan with GBS hyaluronidase significantly reduces TNF-α stimulation by hyaluronan.
Figure 8:
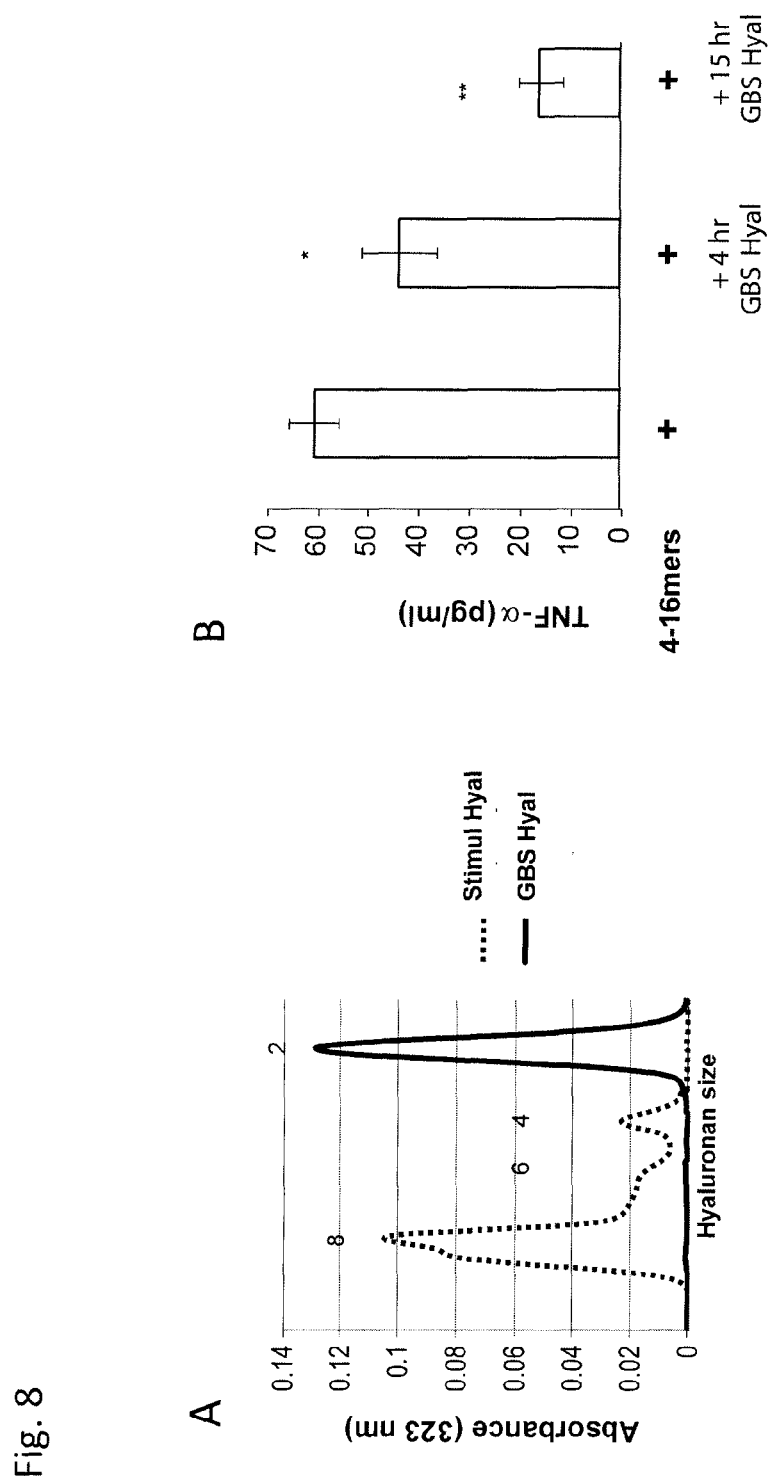
FIG. 8 depicts, in accordance with an embodiment of the invention, GBS hyaluronidase reduces hyaluronan to dimers and dampens inflammation. HPLC profile of hyaluronan fragments generated by bovine hyaluronidase versus Group B *streptococcus* (GBS) hyaluronidase (A). Stimulatory hyaluronan fragments (4-16mers) were digested with GBS hyaluronidase for 4 or 15 hours (B). GBS hyaluronidase digestion leads to reduces cytokine production (B).
Figure 9:
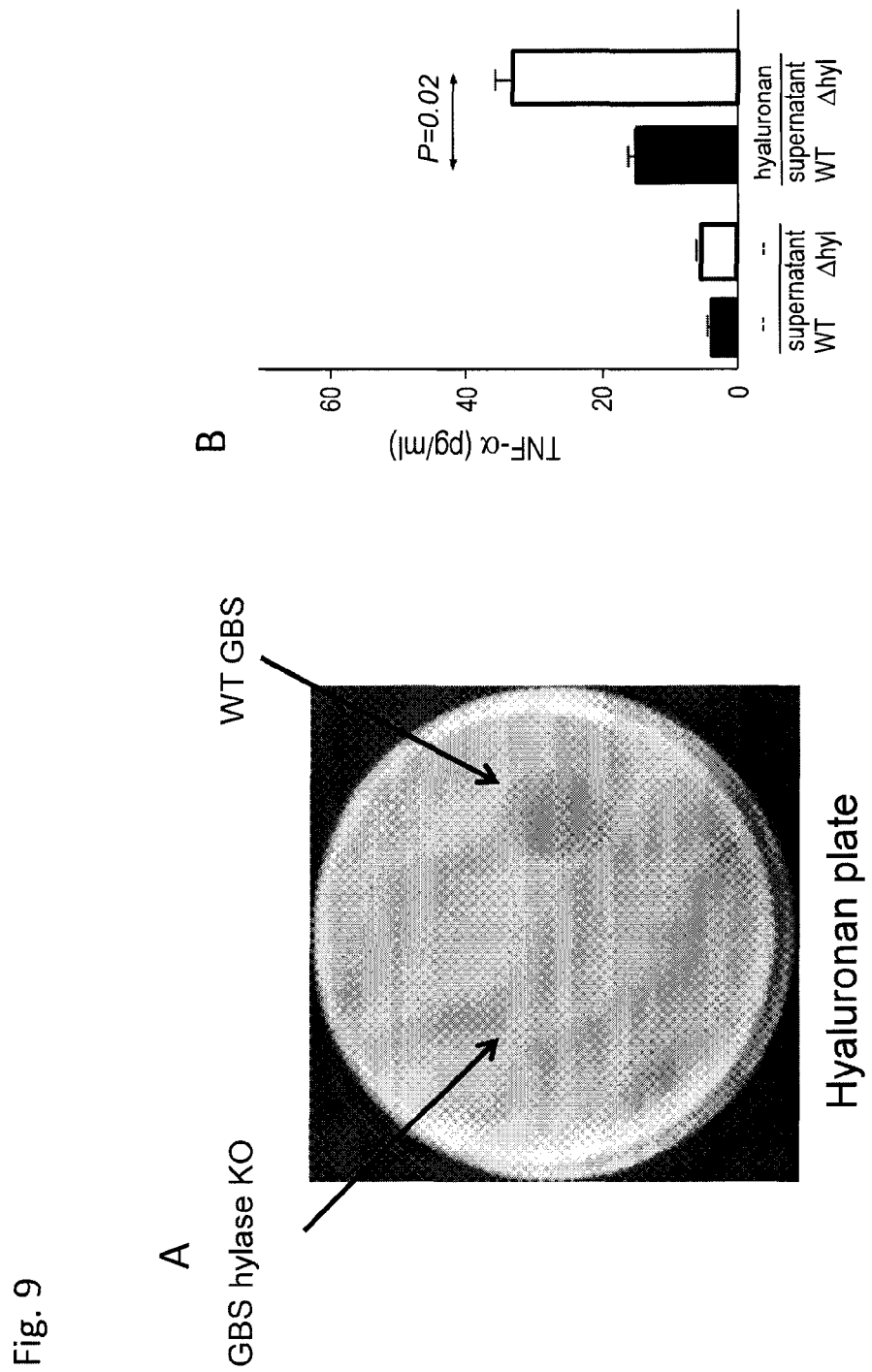
FIG. 9 depicts, in accordance with an embodiment of the invention, degradation of hyaluronan by GBS hyaluronidase leads to decreased TNF-α. WT and GBS hyaluronidase KO show different hyaluronidase activity as evidenced by clearance of hyaluronan (A). Overnight supernatants of the WT and KO bacteria were incubated with high molecular weight hyaluronan (B). The breakdown products were used to stimulate bone marrow derived macrophages (B).
Figure 10:
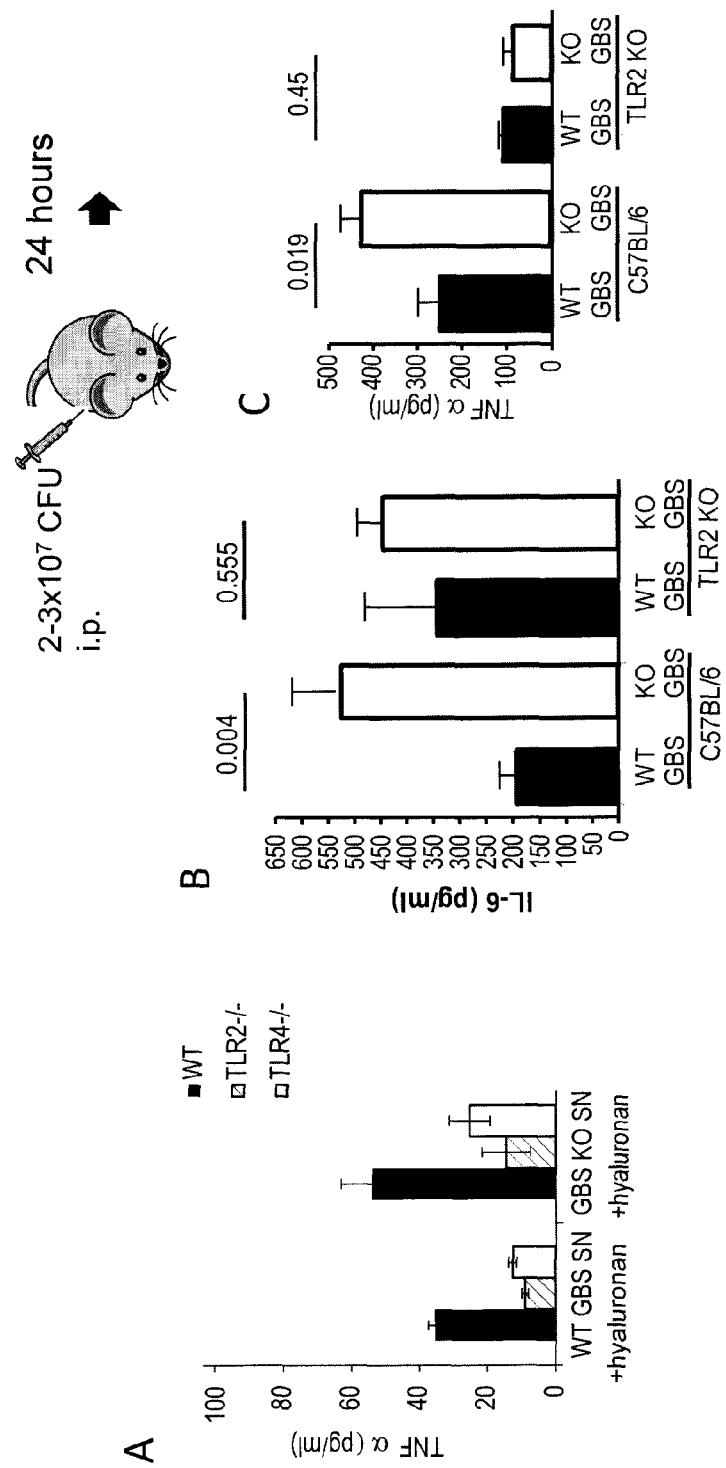
FIG. 10 depicts, in accordance with an embodiment of the invention, HA induced inflammation is dependent on TLR2 and TLR4. Bone marrow derived macrophages from WT, TLR2, and TLR4 KO mice were incubated with hyaluronan predigested with supernatant from WT or hyaluronidase KO GBS, or medium control (A). TNF-α at 24 h was measured. WT and TLR2 KO mice were infected i.p. with $2\text{-}3\times10^7$ WT or KO GBS, and cytokines were measured from the spleen at 24 h (B and C).
Figure 11:
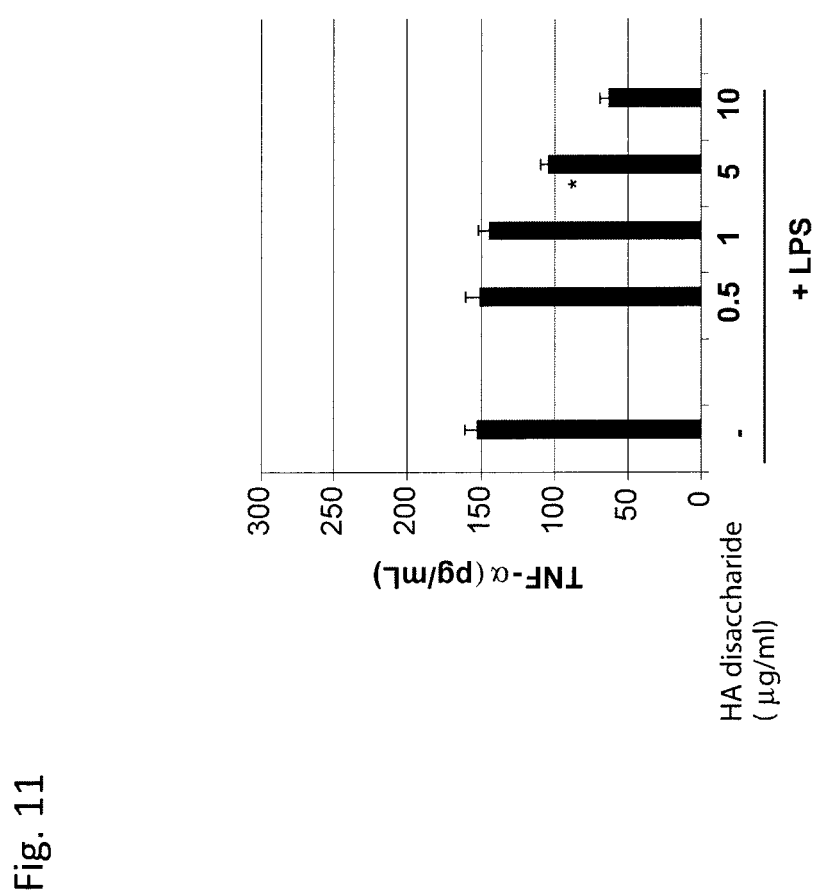
FIG. 11 depicts, in accordance with an embodiment of the invention, hyaluronan dimers are not inert. Bone marrow derived macrophages from WT mice were incubated with LPS and various concentrations of hyaluronan disaccharide. TNF-α at 18 h was measured.
Figure 12:
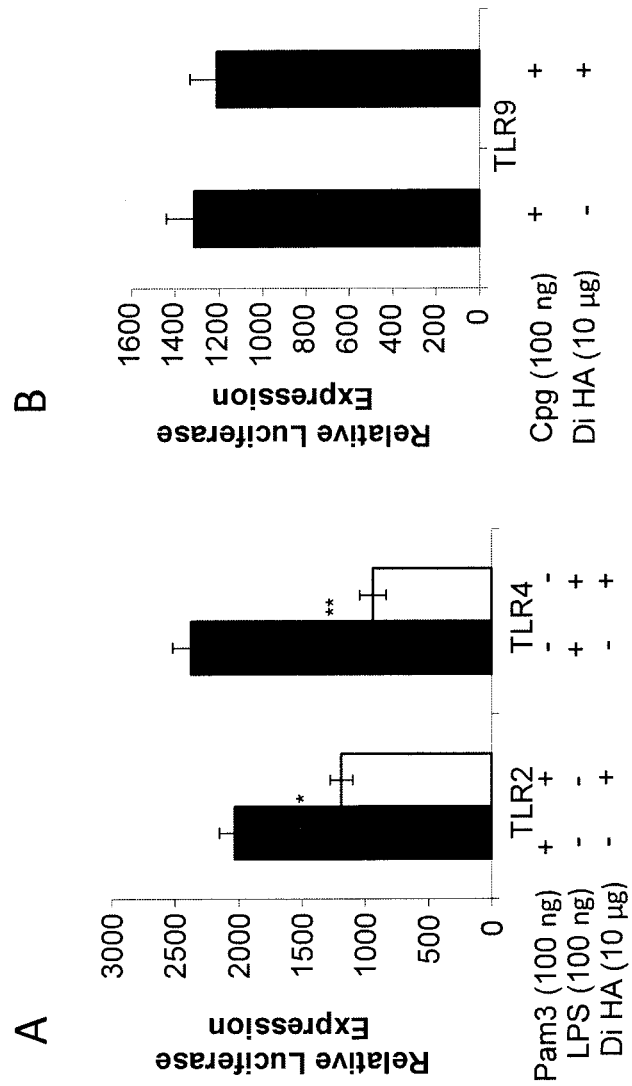
FIG. 12 depicts, in accordance with an embodiment of the invention, HA disaccharide reduces TLR 2 and 4 (A), but not TLR9 (B) signaling. HEK cells were transfected with TLR2, 4, and 9 reporter constructs. The cells were incubated with TLR2 agonist (Pam3), TL4 agonist (LPS), or TLR9 agonist (Cpg) with or without hyaluronan disaccharide. Activation of the reporter genes at 4 h was measured.
Figure 13:
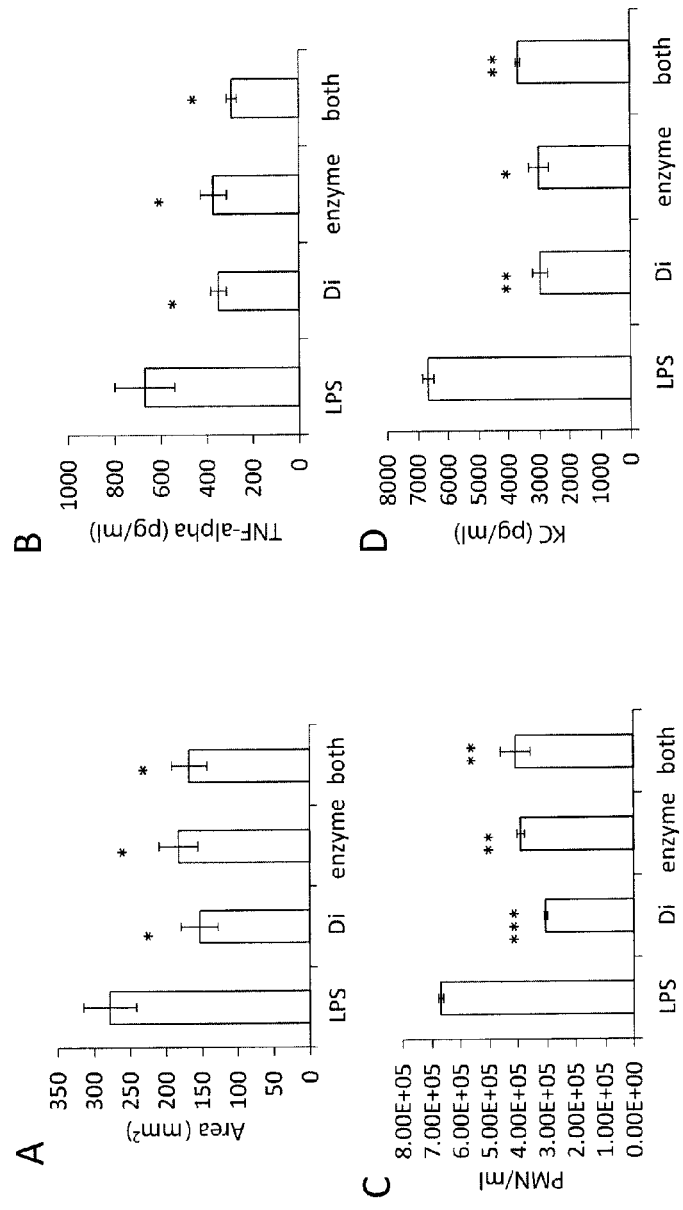
FIG. 13 depicts, in accordance with an embodiment of the invention, the effect of HA disaccharide on lesion formation. Mice were injected subcutaneously with 200 micrograms of LPS with or without 100 micrograms of hyaluronan disaccharide, 1 mg GBS hyaluronidase, or combination of disaccharide and enzyme. The mice were sacrificed after 24 h. "KC" (CXCL1) is a murine homologue of IL-8.
Figure 14:
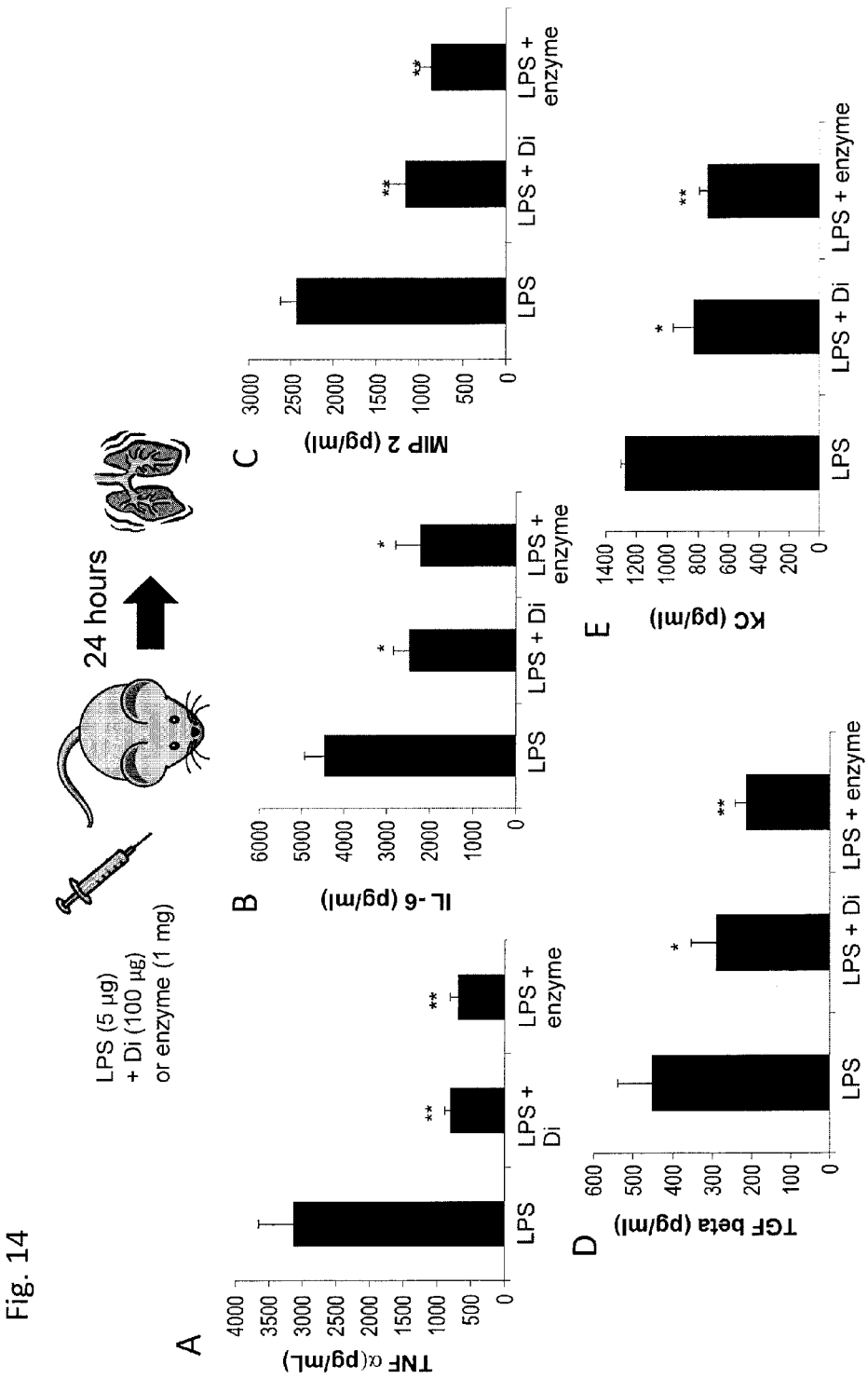
FIG. 14 depicts, in accordance with an embodiment of the invention, HA disaccharide decreases acute lung injury. Mice were injected intratracheally with 5 micrograms of LPS, along with PBS, Hyaluronan disaccharide (100 micrograms) or GBS enzyme (1 mg). At 24 h, the mice were sacrificed and the lungs were analyzed for histology (F&G) and cytokines and chemokines (A-E).
Figure 14:
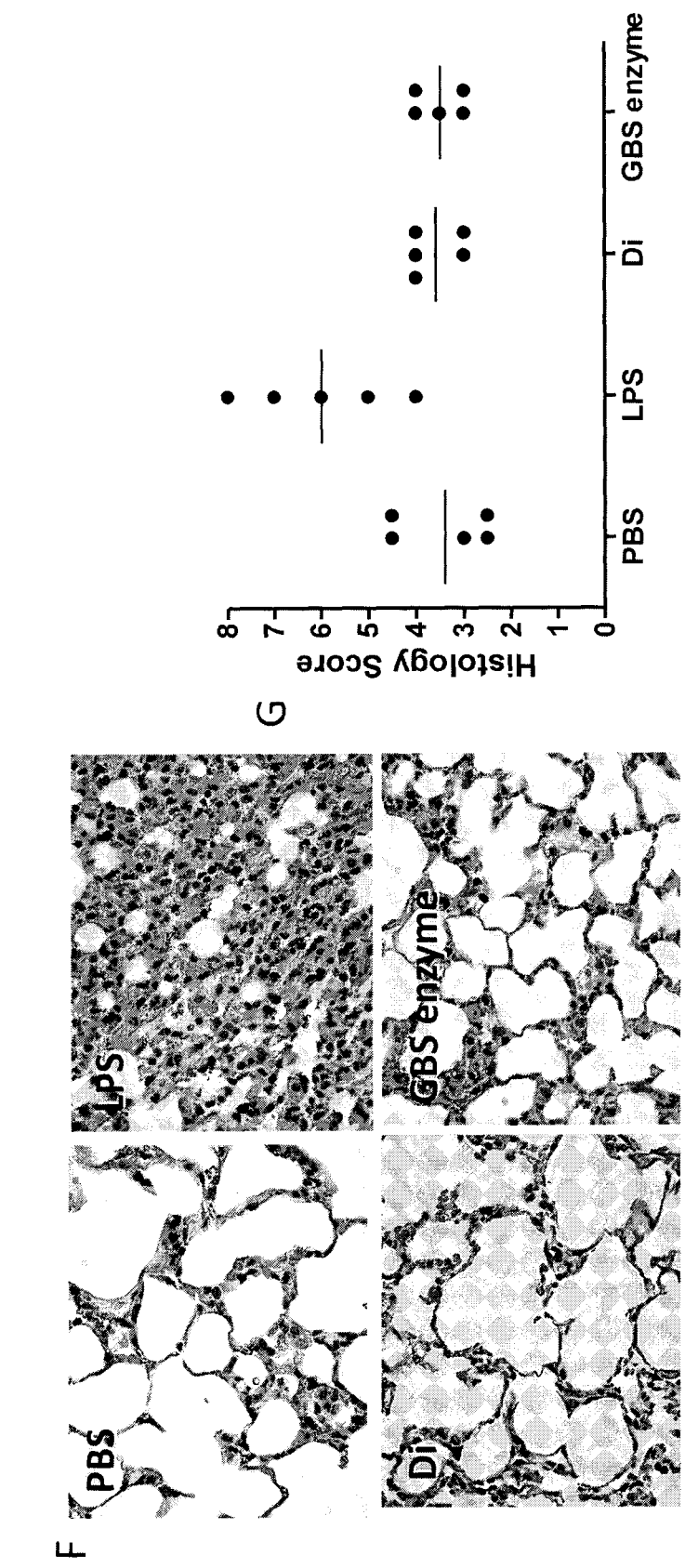

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* $22^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* $3^{rd}$ ed., revised ed., J. Wiley & Sons (New York, N.Y. 2006); Smith, *March's Advanced Organic Chemistry Reactions, Mechanisms and Structure* $7^{th}$ ed., J. Wiley & Sons (New York, N.Y. 2013); Singleton, *Dictionary of DNA and Genome Technology* $3^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, certain terms are defined below.

As used herein, "beneficial results" may include, but are in no way limited to, lessening or alleviating the severity of a disease condition, preventing a disease condition from worsening, curing a disease condition, preventing a disease condition from developing, lowering the chances of a subject developing a disease condition, and prolonging a subject's life or life expectancy.

"Conditions" and "disease conditions," as used herein, may include but are in no way limited to pulmonary fibrosis, sarcoidosis, asthma, chronic obstructive pulmonary disease (COPD), respiratory distress syndrome, bleomycin-induced alveolitis, glomerulonephritis, diabetes, lupus nephritis, renal insufficiency, rheumatoid arthritis, arthritis, spinal injury, brain ischemia, inflammatory atherosclerosis, hepatitis, cirrhosis, inflammation due to tissue rejection, inflammation due to tissue injury, and acne. Additional representative conditions are described in Jiang et al. Physiol Rev 91:221-264, 2011, which is incorporated herein by reference in its entirety as though fully set forth. "Conditions" and "disease conditions" further include bacterial, fungal, and parasitic infections.

"Mammal" as used herein refers to any member of the class Mammalia, including, without limitation, humans and nonhuman primates such as chimpanzees and other apes and monkey species; farm animals such as cattle, sheep, pigs, goats and horses; domesticated mammals, such as dogs and cats; laboratory animals including rodents such as mice, rats and guinea pigs, and the like. The term does not denote a particular age or sex. Thus, adult and newborn subjects, whether male or female, are intended to be included within the scope of this term.

"Treatment" and "treating," as used herein refer to both therapeutic treatment and prophylactic or preventative measures, wherein the object is to slow down (lessen) the inflammatory condition, prevent the inflammatory condition, pursue or obtain beneficial results, or lower the chances of the individual developing the inflammatory condition, even if the treatment is ultimately unsuccessful. "Treatment" and "treating," also refers to both therapeutic treatment and prophylactic or preventative measures, wherein the object is to slow down (lessen) an infection, prevent an infection, pursue or obtain beneficial results, or lower the chances of the individual developing an infection (especially a deep seated infection), even if the treatment is ultimately unsuccessful. Those in need of treatment include those already with the condition, as well as those prone to have the condition or those in whom the condition is to be prevented.

As briefly described above, hyaluronans (HA) are ubiquitous macromolecules that play an important role in normal physiology, as well as pathologic conditions. During tissue destruction, HA is broken down either by direct injury or by the induced activity of host hyaluronidases, and the HA fragments go on to activate the immune system via (at least) Toll-Like Receptor (TLR) 2 and 4. For host defense against infection, this may be a strategy that ties bacterial penetration of deep tissues with activation of the host endogenous immune sensing mechanism. Major Gram-positive pathogens such as Group B *Streptococcus* (GBS) and *Staphylococcus aureus* secrete hyaluronidases to facilitate tissue invasion. It has been hypothesized that these hyaluronidases would further contribute to the activation of the host surveillance system, and this appears to be supported by published findings that hyaluronidases derived from mammals and bacteria (*Streptomyces*) are both immunostimulatory. However, phylogenetic analyses reveal a surprising divergence of hyaluronidases from environmental non-pathogens (e.g. *Streptomyces hydrolyticus, S. coelicolor*) and major pathogens (e.g. GBS, *S. pneumoniae, S. aureus*). The inventors' recent studies have shown that hyaluronidase from GBS, unlike hyaluronidase from *Streptomyces*, down-regulates host pro-inflammatory cytokines and promotes survival of the pathogen during infection. The inventors' research has also demonstrated that the mechanism underlying the immunomodulatory activity lies in the size of the HA degradation fragments. As indicated above, unlike mammalian and *Streptomyces* hyaluronidases, which degrade HA to fragment sizes (4-16mers) that favor activation of TLR pathways, GBS hyaluronidase degrades HA to a disaccharide fragment. It has recently been determined that this fragment size inhibits pro-inflammatory cytokine secretion.

In short, a number of major pathogens have evolved hyaluronidases that destroy the immune activating hyaluronan signal without compromising the ability of the enzymes to facilitate dissemination. By contrast, hyaluronidases from non-pathogens (environmental) are under no selective pressure and therefore can retain their pro-inflammatory properties ("inflammatory hyaluronidases"). A number of opportunistic pathogens that induce deep seated infections in non-immunocompromised hosts express hyaluronidases that are anti-inflammatory. After considering the results of the experiments described herein, the inventors established several therapeutic compositions and strategies.

In some embodiments, the invention teaches a method for treating and/or inhibiting and/or lessening the severity of and/or promoting the prophylaxis of an inflammatory condition in a subject. In various embodiments, the method includes administering a therapeutically effective amount of a composition to the subject, wherein the composition includes a hyaluronan disaccharide and/or a hyaluronidase that is capable of producing a hyaluronan disaccharide when combined with a quantity of hyaluronan. In some embodiments, the hyaluronidase used in the inventive method produces hyaluronan disaccharide via processive degradation of a longer chain of hyaluronan. Merely by way of non-limiting example, the hyaluronidase can be produced by Group B *Streptococcus* (GBS), Group A *Streptococcus, S. aureus, S. pneumoniae, E. faecalis*, and *P. prevotii*. Additional organisms that may produce the hyaluronidase include *B. fragilis, P. aeruginosa, E. coli, C. albicans*. Although certain bacteria with hyaluronidases capable of producing hyaluronan disaccharide are specifically named above, one of skill in the art would readily appreciate that many other types of bacteria (and other organisms) possess the same capability. Therefore, the use of alternative naturally occurring hyaluronidases with similar structural and/or functional properties to those possessed by the bacteria named above is intended to be within the scope of the inventive method. Additionally, one of skill in the art would readily appreciate that by performing mutagenesis on hyaluronidases of mammals, or other microbes, one could construct hyaluronidases that have properties similar to the hyaluronidases from the above list of bacteria. Therefore, the inventive method includes the use of any hyaluronidase (or hyaluronidases) with the aforementioned anti-inflammatory properties, regardless of how they are obtained or produced. Furthermore, the inventive method is not strictly limited to the use of hyaluronidases with anti-inflammatory properties, as one of skill in the art would readily appreciate that alternative enzymes, and other substances, that are structurally and/or functionally similar to those described above could also be used to achieve substantially similar results. In some embodiments, analogs, derivatives, salts or otherwise structurally similar substances to hyaluronan disaccharide are used in the therapeutic methods described herein. In a preferred embodiment, the inflammatory condition treated by the inventive method is acne. In a preferred embodiment, the inflammatory condition treated by the inventive method is caused by *P. acnes*.

In some embodiments, an inhibitor of an inflammatory hyaluronidase is administered to a subject in order to alleviate an inflammatory condition described herein. In some embodiments, the inflammatory condition is any inflammatory condition described herein. In some embodiments, the hyaluronidase inhibitor is an inhibitor of *P. acnes* hyaluronidase. In some embodiments, the inflammatory condition is chronic. In certain embodiments, the inflammatory condition is acute.

In various embodiments, the invention teaches a method for treating and/or inhibiting and/or promoting the prophylaxis of and/or lessening the severity of an infection in an individual caused by a pathogen (opportunistic or otherwise), including administering a therapeutically effective amount of a composition that inhibits a hyaluronidase produced by the pathogen to the individual. Merely by way of non-limiting example, the infection treated by the inventive method can be caused by one or more organism including Group B *Streptococcus* (GBS), Group A *Streptococcus, S. aureus, S. pneumoniae, E. faecalis, P. prevotii, S. mutans*, and *C. difficile*.

In some embodiments, the invention teaches a method for inducing inflammation in a subject, in order to promote healing or an immune response. In some embodiments, the method includes administering a therapeutically effective amount of hyaluronan of a size that induces inflammation (as described herein) to the subject. In some embodiments, the method includes administering a hyaluronidase that degrades hyaluronan into a size that induces inflammation to the subject.

In certain embodiments, the invention teaches a composition for treating and/or inhibiting and/or promoting the prophylaxis of and/or lessening the severity of an inflammatory condition in a subject. In various embodiments, the composition includes a hyaluronan disaccharide and/or a hyaluronidase capable of producing a hyaluronan disaccharide when combined with a quantity of hyaluronan. In some embodiments, the hyaluronidase produces hyaluronan disaccharide via processive degradation of a longer chain of hyaluronan. In some embodiments, the hyaluronidase is produced by one or more organism including Group B *Streptococcus* (GBS), Group A *Streptococcus, S. aureus, S. pneumonia, E. faecalis*, and *P. prevotii*. In some embodiments, the composition includes an inhibitor of an inflammatory hyaluronidase, alone or combined with hyaluronan disaccharide and/or a hyaluronidase capable of producing a hyaluronan disaccharide. In certain embodiments, the inflammatory condition can include, but is in no way limited to pulmonary fibrosis, sarcoidosis, diabetes, asthma, chronic obstructive pulmonary disease (COPD), respiratory distress syndrome, bleomycin-induced alveolitis, glomerulonephritis, lupus nephritis, renal insufficiency, rheumatoid arthritis, arthritis, spinal injury, brain ischemia, inflammatory atherosclerosis, hepatitis, cirrhosis, inflammation due to tissue rejection, inflammation due to tissue injury, acne and combinations thereof. In a preferred embodiment, the inflammatory condition is acne.

In various embodiments, the invention teaches a composition for treating and/or inhibiting and/or promoting the prophylaxis of an infection in an individual caused by a pathogen (opportunistic or otherwise). In some embodiments, the composition includes a hyaluronidase inhibitor that inhibits a hyaluronidase produced by the pathogen. Merely by way of non-limiting example, the infection can be caused by one or more organism including Group B *Streptococcus* (GBS), Group A *Streptococcus, S. aureus, S. pneumoniae, E. faecalis, P. prevotii, S. mutans*, and *C. difficile*.

In some embodiments, the invention teaches a composition for inducing inflammation in a subject, in order to promote healing or an immune response. In some embodiments, the composition includes hyaluronan of a size that induces inflammation and/or a hyaluronidase that degrades hyaluronan into a size that induces inflammation, as described herein.

The ensuing embodiments include examples of compositions. In these examples, the percentages listed are by weight of the composition.

In some embodiments, the hyaluronidase of a composition described herein is between 1% and 100% of the total active ingredients of the composition. In some embodiments, the hyaluronidase is between 5% and 90% of the total active ingredients. In some embodiments, the hyaluronidase is between 10% and 80% of the total active ingredients. In some embodiments, the hyaluronidase is between 20% and 70% of the total active ingredients. In some embodiments, the hyaluronidase is between 30% and 60% of the total active ingredients. In some embodiments, the hyaluronidase is between 40% and 50% of the total active ingredients.

In some embodiments, the hyaluronan of a composition described herein, including hyaluronan disaccharide, or larger fragments, is between 1% and 100% of the total active ingredients of the composition. In some embodiments, the hyaluronan is between 5% and 90% of the total active ingredients. In some embodiments, the hyaluronan is between 10% and 80% of the total active ingredients. In some embodiments, the hyaluronan is between 20% and 70% of the total active ingredients. In some embodiments, the hyaluronan is between 30% and 60% of the total active ingredients. In some embodiments, the hyaluronan is between 40% and 50% of the total active ingredients.

In some embodiments, the hyaluronidase inhibitor of a composition described herein is between 1% and 100% of the total active ingredients of the composition. In some embodiments, the hyaluronidase inhibitor is between 5% and 90% of the total active ingredients. In some embodiments, the hyaluronidase inhibitor is between 10% and 80% of the total active ingredients. In some embodiments, the hyaluronidase inhibitor is between 20% and 70% of the total active ingredients. In some embodiments, the hyaluronidase inhibitor is between 30% and 60% of the total active ingredients. In some embodiments, the hyaluronidase inhibitor is between 40% and 50% of the total active ingredients.

In various embodiments, one or more compositions or compounds disclosed herein and used in conjunction with the inventive methods may be provided as a pharmaceutical composition, including a pharmaceutically acceptable excipient along with a therapeutically effective amount of one or more of the compounds or compositions described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal"

administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions, suspensions, or other cosmetic products. They can also be in the form of microspheres or nanospheres or lipid vesicles or polymer vesicles or polymer patches and hydrogels allowing controlled release. These topical-route compositions can be either in anhydrous form or in aqueous form depending on the clinical indication.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting one or more compositions or molecules of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of syrup, elixir, emulsion or an aqueous or non-aqueous suspension. Such a liquid formulation may be administered directly p.o. or filled into a soft gelatin capsule.

The pharmaceutical compositions and molecules according to the invention may be delivered in a therapeutically effective amount. The precise therapeutically effective amount is that amount of the composition or molecule that will yield the most effective results in terms of efficacy of treatment in a given subject. This amount will vary depending upon a variety of factors, including but not limited to the characteristics of the therapeutic composition or molecule (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a composition or molecule and adjusting the dosage accordingly. For additional guidance, see Allen et al., *Remington: The Science and Practice of Pharmacy* $22^{nd}$ ed., Pharmaceutical Press (Sep. 15, 2012).

Typical dosages of an effective amount of any of the compositions or molecules described herein can be as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method.

In some embodiments, a therapeutic dosage range of hyaluronan disaccharides is between 0.01 and 10000 mg every 6-24 hours, when administered topically to treat an inflammatory skin condition, such as acne. In some embodiments, a therapeutic dosage range of hyaluronan disaccharides is between 0.001 and 100 mg/kg every 6-24 hours, when administered via the enteral route to treat an inflammatory condition. In some embodiments, a therapeutic dosage range of hyaluronan disaccharides is between 0.001 and 100 mg/kg every 6-24 hours, when administered via the parenteral route to treat an inflammatory condition.

In some embodiments, a therapeutic dosage range of a hyaluronidase that produces disaccharides of hyaluronan is between 0.001 and 100 mg every 6-24 hours, when administered topically to treat an inflammatory skin condition, such as acne. In some embodiments, a therapeutic dosage range of a hyaluronidase that produces disaccharides of hyaluronan is between 0.001 and 100 mg/kg every 6-24 hours, when administered via the enteral route to treat an inflammatory condition. In some embodiments, a therapeutic dosage range of a hyaluronidase that produces disaccharides of hyaluronan is between 0.001 and 100 mg/kg every 6-24 hours, when administered via the parenteral route to treat an inflammatory condition.

In some embodiments, a therapeutic dosage range of a hyaluronidase that produces hyaluronan of a size that induces inflammation is between 0.001 and 100 mg every 6-24 hours, when administered topically to treat an infection. In some embodiments, a therapeutic dosage range of a hyaluronidase that produces hyaluronan of a size that induces inflammation is between 0.001 and 100 mg/kg every 6-24 hours, when administered via the enteral route to treat an infection.

In some embodiments, a therapeutic dosage range of a hyaluronidase inhibitor is between 0.01 and 10000 mg every 6-24 hours, when administered topically to treat an inflammatory skin condition, such as acne, or an infection of the skin. In some embodiments, a therapeutic dosage range of a hyaluronidase inhibitor is between 0.001 and 100 mg/kg every 6-24 hours, when administered via the enteral route to treat an infection. In some embodiments, a therapeutic dosage range of a hyaluronidase inhibitor is between 0.001 and 100 mg/kg every 6-24 hours, when administered via the parenteral route to treat an infection.

The present invention also teaches a kit directed to one or more of: treating, inhibiting, promoting the prophylaxis of, preventing, alleviating the symptoms of, and reducing the likelihood of inflammatory disease or infection (such as any of those described herein), in a mammal in need thereof. The kit is an assemblage of materials or components, including at least one of the inventive compositions or molecules described herein. Thus, in some embodiments the kit contains a composition including one or more hyaluronan disaccharides, and/or a hyaluronidase produced by an organism that can include, but in no way limited to, Group B *Streptococcus* (GBS), Group A *Streptococcus, S. aureus, S. pneumoniae, E. faecalis*, and *P. prevotii*. Additional organisms that may produce the hyaluronidase include *B. fragilis, P. aeruginosa, E. coli*, and *C. albicans*. In certain embodiments, the kit also or alternatively contains an inhibitor of a hyaluronidase produced by any of the aforementioned organisms, or any other pathogens that depend, at least in part, on hyaluronidase for tissue invasion and/or host immune system evasion. The kit may alternatively contain one or more analog, derivative, salt, synthetic version or pharmaceutical equivalent of the hyaluronan disaccharides or hyaluronidases described herein.

The exact nature of the components configured in the inventive kit depends on its intended purpose. By way of non-limiting example, some embodiments are configured for one or more purpose selected from: treating, inhibiting, promoting the prophylaxis of, preventing, alleviating the symptoms of, and/or reducing the likelihood of one or more inflammatory conditions or infections. In one embodiment, the kit is configured particularly for the purpose of treating mammalian subjects. In another embodiment, the kit is configured particularly for the purpose of treating human subjects. In another embodiment, the kit is configured for treating adolescent, child, or infant human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as treating, inhibiting, promoting the prophylaxis of and/or preventing, alleviating the symptoms of, reducing the likelihood of, or inhibiting inflammatory conditions or infections using the appropriate compositions and methods described herein. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions, molecules and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be one or more glass vials or plastic containers used to contain suitable quantities of an inventive composition disclosed herein. The packaging material generally has an external label which indicates the contents and/or purpose of the kit and/or its components.

One skilled in the art will recognize many methods and materials similar or equivalent to those described herein, which could be used in the practice of the present invention. Indeed, the present invention is in no way limited to the methods and materials described.

EXAMPLES

Example 1

Hyaluronan, General Physiology, and Pathogenesis

HA is a linear glycosaminoglycan with a molecular weight greater than 5,000 Da. The polymer is found ubiquitously in the extracellular matrix in nearly all tissues, and is synthesized by many cell types including fibroblasts, endothelial cells, and keratinocytes. Its primary and most obvious function is to contribute towards the stability and structure of the extracellular matrix, but a broad literature also suggests its involvement in a number of other physiologic and pathologic conditions including cancer, atherosclerosis, pulmonary fibrosis, pulmonary emphysema, nephritis, arthritis, cerebral infarct, and diabetes.

Example 2

Hyaluronan and Immunity

Recent studies implicate a new and different role for HA turnover. Several studies have now shown that HA is rapidly degraded during injury by nonspecific damage and self hyaluronidases. The HA breakdown products then activate TLR innate immune signaling that triggers robust inflammation, alerts the host to danger, and mobilizes, directs, and coordinates the more general host defense forces of both innate and acquired immunity. On activation of TLR2, TLR4, or downstream adapter protein Myd88 through the NF-κB activation pathway, cytokines and chemokines are triggered, and neutrophils recruited to the scene of tissue destruction. This injury-linked immune activation is thought to represent an effective way to alert the body to the possible presence of "danger." Hence, this "endogenous" defense mechanism may complement the more direct pathogen detection mechanisms whereby TLRs and other pattern recognition receptors recognize molecules or molecular motifs produced only by microbes.

Example 3

Bacterial Hyaluronidases

Hyaluronidases are synthesized not only by the host, but are also widely expressed by eukaryotes, parasites, fungi, and bacteria. Bacterial hyaluronidases (also termed hyaluronan lyase or hyase) are believed to be essential for bacterial dissemination through tissues or for extraction of nutrients during starvation. Therefore linking pathogen tissue destruction and dissemination with immune activation is a useful and important process used by the host to detect and fight infections. So it is only to be expected that effective pathogens would have found a way to circumvent this problem.

Example 4

A Novel Immune Evasion Mechanism of Bacterial Hyaluronidases

The inventors generated an allelic exchange mutant of the hyaluronidase gene in the invasive pathogen *S. agalactiae* (also known as GBS). The inventors then compared the ability of WT and isogenic GBS mutants to cause infection and inflammation in a murine model of sepsis. The inventors' data show that in the absence of hyaluronidase, ΔHylA GBS induced higher levels of pro-inflammatory cytokines (IL-6, TNF-α), were more readily cleared by the host, but also induced higher host mortality (FIG. 2). These findings are consistent with the interpretation that GBS hyaluronidase has anti inflammatory properties that promote survival of the pathogen.

Example 5

Immunomodulatory Mechanisms of GBS Hyaluronidase

Previously published studies have established that hyaluronidases synthesized by environmental microbes, *Streptomyces*, degrade HA to fragment sizes of 4-16mers, which have been shown to activate the TLR2 or TLR4 immune pathway. By contrast, GBS hyaluronidase degrades HA to a single product—a disaccharide (FIG. 3A) that has no immunostimulatory capacity (FIG. 3C). Consistent with these findings, the inventors found that HA+WT GBS induces lower levels of TNF-α compared to HA+bovine hyaluronidase or HA+ΔHylA GBS in a macrophage stimulation assay (FIG. 3B). Since bovine hyaluronidase degrades HA to 4-16mers, the inventors asked whether subsequent degradation with GBS hyaluronidase would abrogate induction of TNF-α. Indeed that is what the inventors found (FIG. 3B right). Because the major product of GBS hyaluronidase enzymatic activity is diHA (disaccharide), the inventors also evaluated the direct effect of DiHA on TNF-α secretion induced by a TLR2 agonist Pam3csk4. The inventors showed that diHA partially inhibited Pam3csk4 induced TNF-α secretion (FIG. 3C).

The inventors' results indicate that *Streptomyces* and GBS hyaluronidases induce different HA fragmentation patterns, which lead respectively to activation and suppression of the host TLR sensing mechanism. Consistent with this conclusion, the inventors showed that in WT mice, WT GBS induces lower levels of TNF-α and IL-6 compared to ΔhylA GBS, but this difference is significantly reduced in TLR2−/− mice (FIG. 4).

Example 6

Different Hyaluronidase Structure Function for Gram-Positive Pathogens and Environmental Non-Pathogens—Evolutionary Implications GBS is a human pathogen that causes invasive diseases of newborns. *Streptomyces*, by contrast, are environmental bacteria, that do not usually cause human disease. Hyaluronidases from Gram-negative bacteria are not secreted, and instead are trapped within the periplasmic space. Prior bacterial hyaluronidase studies report that *Streptomyces* hyaluronidases create fragment sizes that are very similar to those produced by mammalian hyaluronidases, but hyaluronidases from GBS and *S. pneumoniae* produce fragments that are strictly disaccharides (See Pritchard et al. 1994. Characterization of the group B *streptococcal* hyaluronate lyase. *Arch Biochem Biophys* 315:431-437; and Ponnuraj, K., and Jedrzejas, M. J. 2000. Mechanism of hyaluronan binding and degradation: structure of *Streptococcus pneumoniae* hyaluronate lyase in complex with hyaluronic acid disaccharide at 1.7 A resolution. *J Mol Biol* 299:885-895, both of which are incorporated by reference herein in their entirety as though fully set forth). Crystal structure analyses strongly suggest that the enzymes from these pathogens undergo processive degradation and do not release the HA fragment until it is fully degraded (See Ponnuraj, K., and Jedrzejas, M. J. 2000. Mechanism of hyaluronan binding and degradation: structure of *Streptococcus pneumoniae* hyaluronate lyase in complex with hyaluronic acid disaccharide at 1.7 A resolution. *J Mol Biol* 299:885-895; and Li, S., and Jedrzejas, M. J. 2001. Hyaluronan binding and degradation by *Streptococcus agalactiae* hyaluronate lyase. *J Biol Chem* 276:41407-41416, both of which are incorporated herein by reference in their entirety as though fully set forth). These biochemical analyses broadly divide bacterial hyaluronidases into two groups: those that generate fragments that are likely to activate TLR signaling, and those that yield HA fragment sizes that are too small to trigger TLR signaling. Interestingly, this proposed classification scheme is also consistent with evidence from the phylogenetic analysis of bacterial hyaluronidases (FIG. 1). Sequence homologies separate hyaluronanidase enzymes into major groupings: those belonging to major Gram-positive pathogens (GBS, *S. pneumoniae*, and *S. aureus*), and those belonging to environmental non-pathogens (*Streptomyces*). Opportunistic pathogens (*E. faecalis*, and *P. prevotii*) fit into a different group.

Example 7

General Approach

After organizing available evidence into a coherent rational framework, the inventors determined that all these clues are not merely a coincidence, but rather reflect the overarching masterwork of evolutionary forces. Specifically, to accomplish a need to invade, evade, and disseminate during infection with great stealth. The inventors concluded that it was very likely that major pathogens such as *S. aureus, S. pneumoniae*, and GBS have acquired hyaluronidases that effectively degrade host HA polymers without alerting the immune system. These pathogenic hyaluronidases could also inhibit inflammation in another way: by degrading pro-inflammatory HA fragments generated by the enzymatic action of host hyaluronidases further into fragments that are too small to activate TLR signaling. Such specification and evolutionary pressure are not so prevalent for organisms such as *Streptomyces*. Therefore they likely retain hyaluronidases that cut more randomly.

Example 8

Purification of Bacterial Hyaluronidases

Hyaluronidases from *S. aureus, S. pneumoniae*, GBS, *E. faecalis*, and *P. prevotii* (and others that could be useful in the inventive compositions and methods) can be purified by using standard published bacterial hyaluronanidase purification protocols (See Pritchard et al. Characterization of the group B *streptococcal* hyaluronate lyase. *Arch Biochem Biophys* 315:431-437; Berry, et al. 1994. Cloning and nucleotide sequence of the *Streptococcus pneumoniae* hyaluronidase gene and purification of the enzyme from recombinant *Escherichia coli. Infect Immun* 62:1101-1108. PMCID:PMC186229; and Tam, Y. C., Chan E. C. 1985 Purification and characterization of hyaluronidase from oral *Peptostreptococcus* species. *Infect Immun.* 47:508-13. PMCID:PMC263200, all of which are incorporated herein by reference in their entirety as though fully set forth). Alternatively, hyaluronidases can be expressed in *E. coli* (e.g. with the use of a HIS tag), and the enzymes can be purified using affinity columns. One of skill in the art would readily appreciate that there are numerous alternative ways to produce and purify hyaluronidases, for the purposes of experimentation and on a commercial scale.

Example 9

Expression of Hyaluronidases

Hyaluronidase from GBS, *S. aureus, S. pneumoniae, E. faecalis, P. prevotii*, and *S. coelicolor* can be expressed in the ΔHylA GBS background. In order to directly compare the enzymatic and immunomodulatory functions of various hyaluronidases, the hyaluronidase genes from GBS, *S. aureus, S. pneumoniae, E. faecalis, P. prevotii*, and *S. coelicolor* can be inserted into an expression vector, which is then introduced into the ΔHylA GBS.

Example 10

Additional Results/Conclusion

As demonstrated herein, the inventors' data indicate that DiHA generated by GBS hyaluronidase has an anti-inflammatory property. The inventors' data also strongly suggests that hyaluronidases from certain pathogens would be able to destroy the TLR stimulating activity of 4-16mers (generated by host hyaluronidase). Furthermore, experiments using WT and ΔHylA GBS in TLR2-/- mice strongly suggest a role for TLR2 in hyaluronidase mediated immunomodulation. In short, the inventors' research demonstrates a link between the immunomodulatory properties of various bacterial hyaluronidases to the HA fragment sizes and to the TLR2 and/or TLR4 immune pathways.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for treating and/or inhibiting an inflammatory condition in a subject, comprising administering a therapeutically effective amount of a composition comprising hyaluronan disaccharide to the subject, wherein the inflammatory condition is acute lung injury, pulmonary fibrosis or acne.

2. The method of claim 1, wherein the inflammatory condition is acute lung injury.

3. The method of claim 1, wherein the inflammatory condition is acne.

4. The method of claim 3, wherein the composition is administered topically.

5. The method of claim 1, wherein the inflammatory condition is pulmonary fibrosis.

6. The method of claim 5, wherein the composition is administered into the respiratory system.

* * * * *